(12) United States Patent
Hogan

(10) Patent No.: US 7,431,453 B2
(45) Date of Patent: Oct. 7, 2008

(54) MODULAR EYEWEAR SYSTEM

(75) Inventor: Martin Hogan, Melbourne (AU)

(73) Assignee: Ophthalmic Engineering Pty Ltd, Malvern (AU)

( * ) Notice: Subject to any disclaimer, the term of this patent is extended or adjusted under 35 U.S.C. 154(b) by 27 days.

(21) Appl. No.: 10/550,120

(22) PCT Filed: Mar. 19, 2004

(86) PCT No.: PCT/AU2004/000347

§ 371 (c)(1),
(2), (4) Date: Jun. 30, 2006

(87) PCT Pub. No.: WO2004/083941

PCT Pub. Date: Sep. 30, 2004

(65) Prior Publication Data

US 2006/0268220 A1   Nov. 30, 2006

(30) Foreign Application Priority Data

Mar. 19, 2003   (AU)   .............................. 2003901272

(51) Int. Cl.
*G02C 1/00*   (2006.01)
(52) U.S. Cl. .............................. 351/158; 351/47; 351/57
(58) Field of Classification Search ............... 351/41, 351/44, 47, 48, 57, 58, 124–139, 158; 359/409
See application file for complete search history.

(56) References Cited

U.S. PATENT DOCUMENTS

| | | | | |
|---|---|---|---|---|
| 6,056,398 A * | 5/2000 | Negishi | ....................... | 351/55 |
| 6,170,949 B1 * | 1/2001 | Mauch | ....................... | 351/47 |
| 6,702,440 B1 * | 3/2004 | Park | ........................... | 351/57 |
| 2002/0140897 A1 * | 10/2002 | Huang | ......................... | 351/57 |
| 2003/0169494 A1 * | 9/2003 | Porter et al. | ................. | 359/409 |

* cited by examiner

*Primary Examiner*—Huy K Mai
(74) *Attorney, Agent, or Firm*—Knoble, Yoshida & Dunleavy LLC

(57) ABSTRACT

A modular eyewear system (700) including magnetic mounting means for releasable magnetic mounting of one or more eyewear elements (710) such as a loupe assembly or a similar magnification system to a frame member for wearing on a wearer's head. Both the frame member and the loupe assembly are provided with complementary magnetic mounting means, whereby the loupe or magnification system is releasably mountable to the frame member. Other elements of the modular system include light delivery means, eyesight correction lenses, protective eyeshields, adjustable nosepieces, optical filter elements, masks and helmets, the system allowing these elements to be used separately or together depending on the desired use.

23 Claims, 13 Drawing Sheets

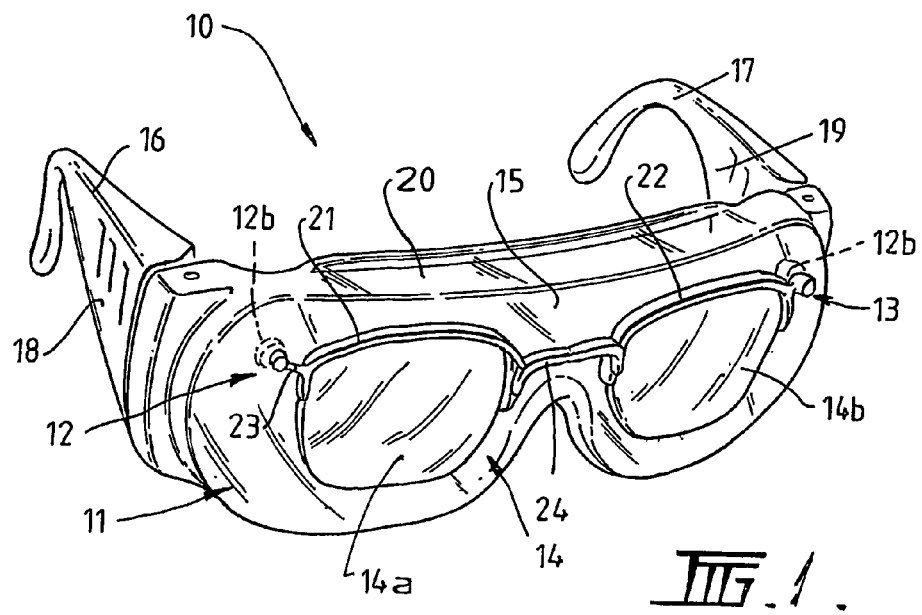
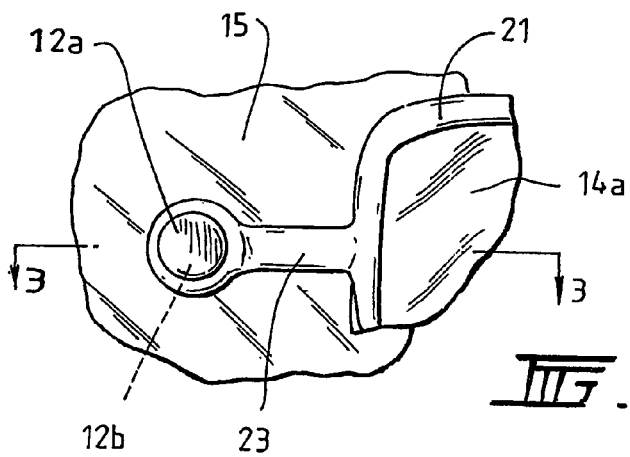
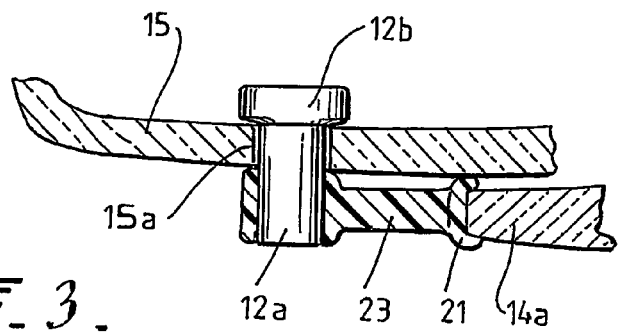

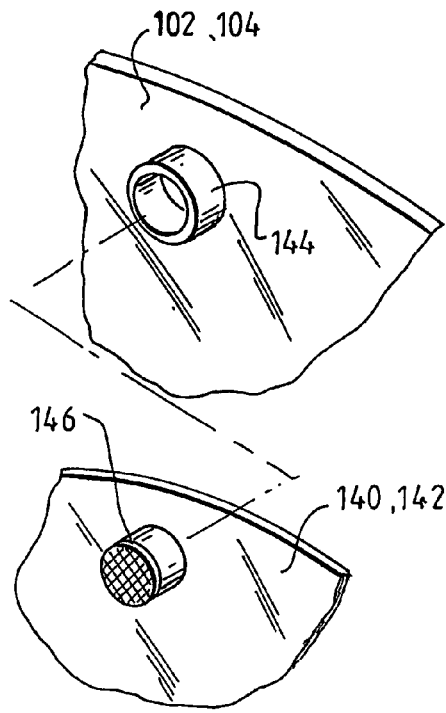
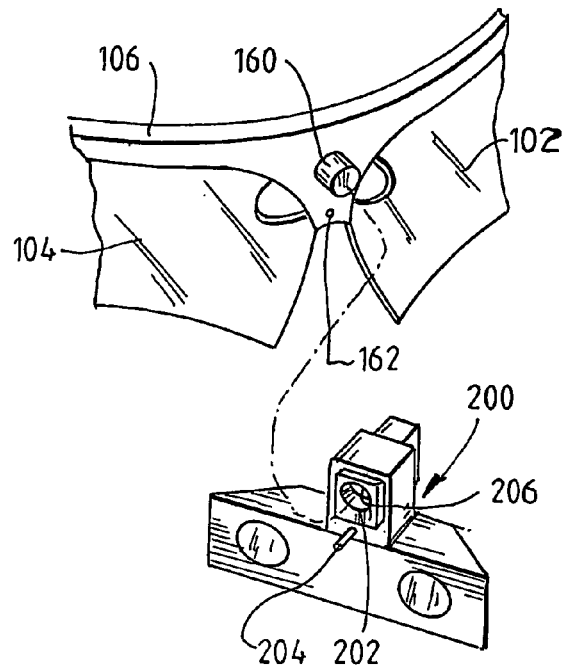
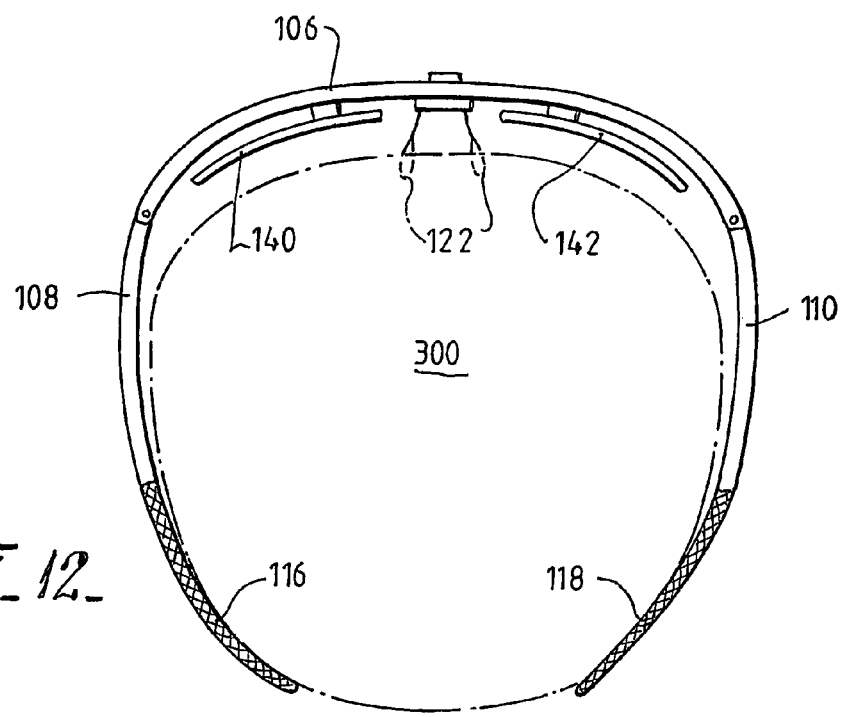
FIG_10.
FIG_11.
FIG_12.

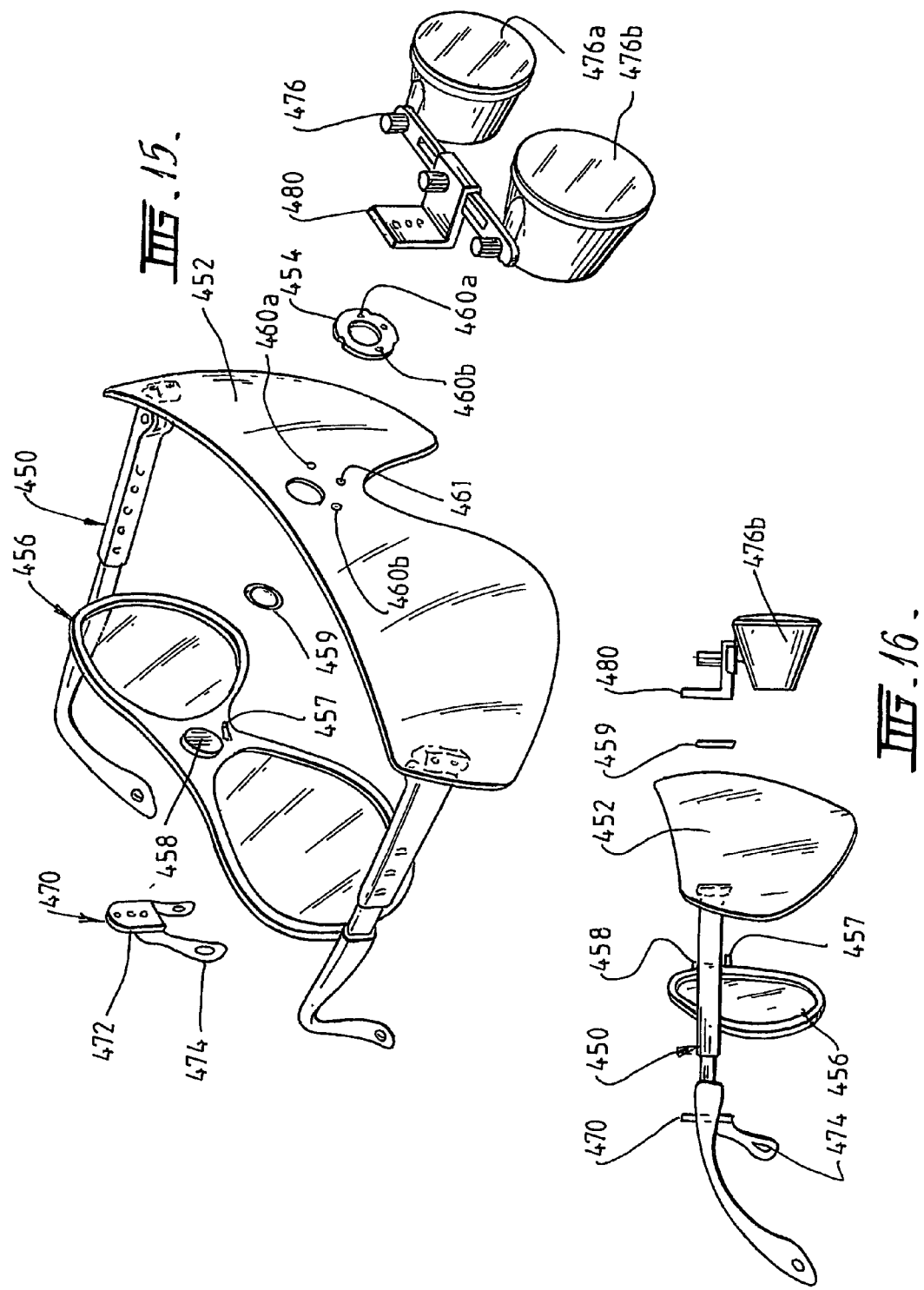

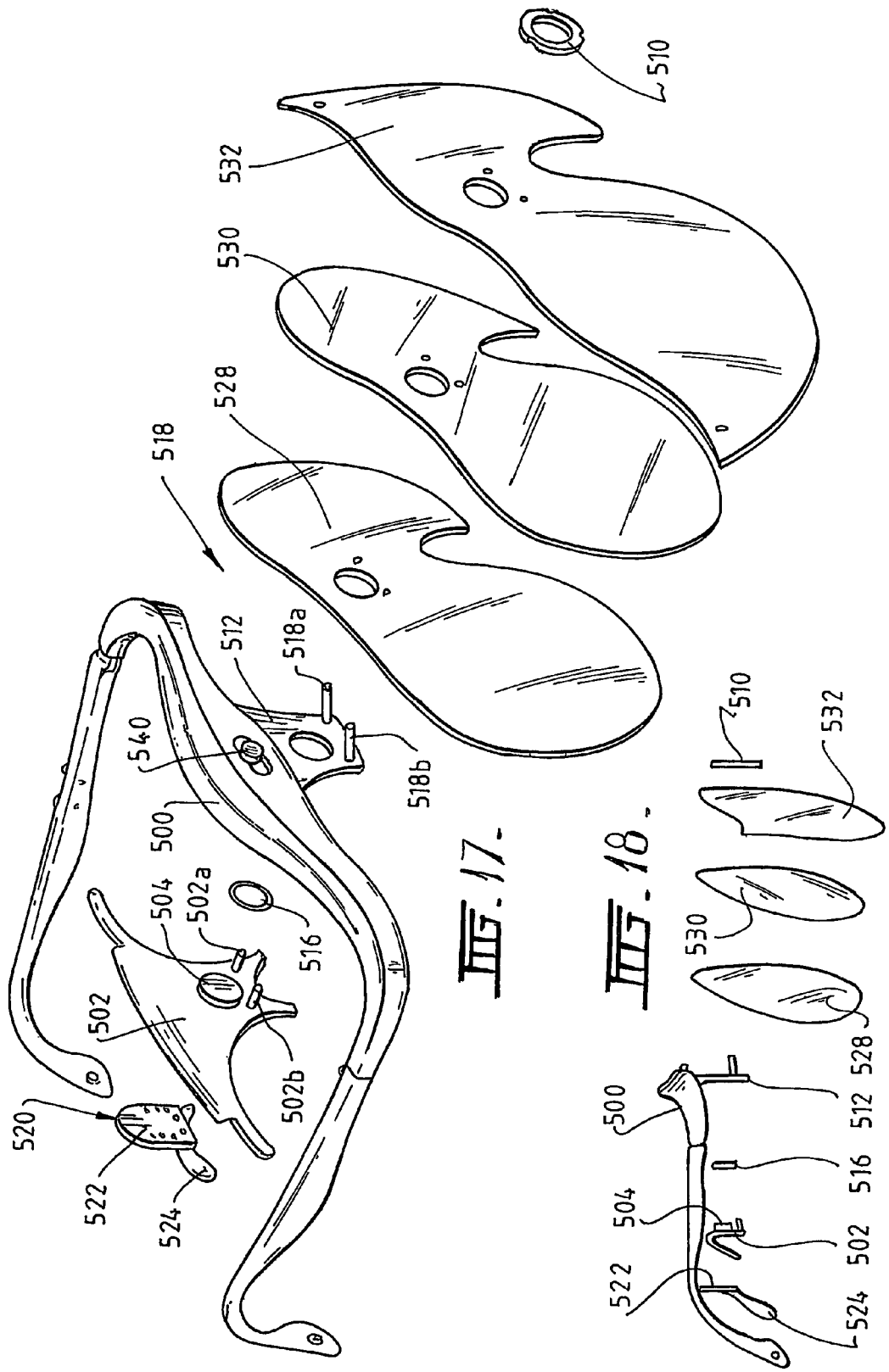

MODULAR EYEWEAR SYSTEM

FIELD OF THE INVENTION

The present invention relates to eyewear. More particularly the present invention relates to a modular eyewear system that can be flexibly adapted for one or more functions including protection against industrial hazards and solar radiation, eyesight correction, and magnification. The modular eyewear system can be used in a variety of environments and for a variety of purposes including work, leisure and sport.

BACKGROUND OF THE INVENTION

In this specification, where a document, act or item of knowledge is referred to or discussed, this reference or discussion is not an admission that the document, act or item of knowledge or any combination thereof was at the priority date: publicly available, known to the public, part of common general knowledge or known to be relevant to an attempt to solve any problem with to which this specification is concerned.

Myriad types of eyewear have been used through the ages to improve eyesight or protect the eyes. For example, prescription lenses in the form of contact lenses or glasses are used to correct sight.

In industrial environments, eye protection is worn to protect the eyes from hazards including flying debris, air or gas jets, grit, sparks, acid splatters and strong energy sources such as welding arcs, lasers, and ultraviolet light. In medical environments, medical professionals such as surgeons and dentists wear protective eyewear to provide protection against entry into the eye of bodily fluids or other potentially infectious or damaging substances from a patient. Surgeons and dentists may also need to use magnification devices or other optical instruments whilst carrying out procedures on patients. Many sporting or leisure pursuits require eye protection. For example scuba divers require face masks to be able to see underwater, whilst skiers require tinted, wrap around glasses or goggles to protect their eyes from wind, particles of snow and UV radiation.

Conventional eyewear worn on the face is typically held in place by a nose piece and a pair of arms for locating the eyewear in known manner on the ears of the wearer.

While eyewear may have multiple functions, it is usually made for a specific purpose. For example, a scuba diver's face mask or skier's goggles may include prescription lenses, but can be used for no other purpose than scuba diving or skiing respectively.

Similarly, eyewear for use in industrial environments usually has no application outside the industrial environment.

This limited functionality of eyewear can be particularly inconvenient in certain applications. For example, a fly fisherman may stand at a river from dawn to dusk, in a wide range of light conditions, requiring several changes of eyewear to different polarizing lenses so that the fish may be seen in different light levels. Given the relatively high cost of a single pair of spectacles, it is not viable for a fisherman to have multiple pairs, each having a different set of polarizing lenses.

Apart from specialist applications such as fly fishing, many people wear spectacles and most have at least two pairs—a prescription pair and prescription sunglasses. They may also have a scuba diving mask with prescription lenses and/or skiing goggles with prescription sunglass lenses.

There is therefore a need for a modular eyewear system that allows the user to readily change eyewear elements, or the combination of eyewear elements according to their various activities and interests, thus dispensing with the need and expense of having multiple pairs of spectacles and other visual aids.

SUMMARY OF THE INVENTION

The present invention provides a modular eyewear system including magnetic mounting means for releasable magnetic mounting of one or more eyewear elements.

Magnetic mounting means according to the invention may take any suitable form. Typically the magnetic mounting means comprises small magnets, such as rare earth magnets. In a preferred embodiment, each of the eyewear elements includes a magnet that can be attracted to, and held firmly by the magnet of another eyewear element, or a magnet located within a protective eyeshield, eyewear frame, or protective headgear.

Existing eyeshields, eyewear frames or protective headgear can be modified to include a magnet of the mounting means. For example the magnet may form part of the frame of prescription spectacles comprising a pair of lens surrounds connected to one another via a brow rail. The brow rail is preferably resiliently deformable, whereby demounting is facilitated by flexing the frames slightly outwardly to create minor deformation of the brow rail which helps to overcome the magnetic attraction as eyewear elements are separated from one another or from the mounting means.

In a preferred embodiment a first eyewear element can be attached to a magnet forming part of a spectacle frame; a magnet of a second eyewear element may be attached to the magnet of the first eyewear element. Subsequent eyewear elements may be similarly attached.

Thus, the present invention provides a convenient, modular system. For example, whilst at home a wearer may employ a bi-focal prescription lens element, when out in the garden they may add a UV filter/polarizing element, while at work the wearer may replace the UV filter/polarizing element with a protective visor element to protect them from chemical splashes.

In a preferred embodiment the magnet may be in the form of a projection, which can be received in a recess in an optical element, or the magnet may be recessed to receive a projection from an optical element.

In one embodiment, the magnetic mounting means comprises a magnetic projection carried by an outer marginal edge of an extended frame of prescription spectacles, the magnetic projection in use extending at least partly through an aperture in the lens of a protective eyeshield element. The eyeshield element may further comprises a magnetic disc positioned on an opposite side of the eyeshield element in the region of the aperture. In this way the user has a prescription lens and an eyeshield located in front of their eyes.

The magnetic mounting means may additionally include a mechanical mounting feature such as a projection in the form of a locating pin that can be received in a recess in an optical component, or a recess that can receive a projection from an optical component, or a combination thereof. This mechanical mounting feature can, for example, prevent movement of the optical component relative to the mounting means or bear part of any load imparted upon the system. The mechanical mounting feature may be moveable within the recess such that an eyewear element can in use be located in different positions relative to the spectacle frame, or other eyewear elements.

According to another aspect of the present invention, there is provided a modular eyewear system including a magnetic mounting means for releasable magnetic mounting of one or more eyewear elements, and a nose support for supporting the protective eyewear on the nose of a wearer, which nose support can be releasably mounted on the magnetic mounting means.

The nose support according to the present invention may comprise nose pads such as are known in the art. The nose pads may project downwardly from a connecting web or bridge piece. The nose piece may be mounted on a bridge piece. When an eyewear element is relatively heavy, such as an optical instrument, the nose pads are preferably of relatively large area so as to reduce the pressure transmitted to the nose of the wearer by the nose pads. The nose piece may be modified so as to be capable of being mounted on the nose portion of a respirator such as a filter-type respirator rather than directly on the wearer's nose.

In a preferred embodiment, the nose support is adjustable in the vertical direction (the vertical direction referring to the orientation of the protective eyewear when the wearer's head is upright). In a preferred embodiment the bridge piece has one or more recesses in which can be located one or more correspondingly shaped pins on an eyewear element, protective eyeshield, eyewear frame, or protective headgear. Where multiple recesses are located vertically along the bridge piece, the position of the pin(s) can be changed to adjust the location of the nose piece in the vertical direction. Alternatively the bridge piece may include a single recess such as a slot so that the position of the pin can be changed by sliding along the slot.

For example, if the nose pad is generally V-shaped, this adjustability allows the eyewear to be capable of fitting persons of different nose width of the nose at the point between the eyes, as this dimension differs considerably from person to person.

This adjustability is also useful for raising or lowering an eyewear element comprising a multifocal lens. In some sports such as shooting, this adjustability is invaluable to ensuring that the shooter is looking through the center of the correct focal length lens at the time of sighting and shooting a target.

In a preferred embodiment, some eyewear elements such as opthalmascopes, and optical loupes adapted for use with the present invention, are adjustable in the vertical direction. In a preferred embodiment such optical elements include a bridge piece which has one or more recesses in which can be located one or more correspondingly shaped pins on an eyewear element, protective eyeshield, eyewear frame, or protective headgear. Where multiple recesses are located vertically along the bridge piece, the position of the pin(s) can be changed to adjust the location of the nose piece in the vertical direction, thus ensuring that the opthalmascope or loupe or other device is correctly positioned relative to the user's eye. Alternatively the recess may comprise a single slot along which the pin(s) may be moved.

In addition to eyewear elements, the modular eyewear system of the present invention may provide for mounting of other elements. For example a nose and/or mouth shield may be magnetically or mechanically mounted to the spectacle frame of eyewear element.

A nose or mouth shield could be used to protect a dental or medical patient from the breath of the dentist or doctor impinging directly upon them. Similarly a nose or mouth shield could protect an industrial worker from splashback from a reaction, or protect a surgeon from being splashed or sprayed by blood. Typically a suitable nose and/or mouth shield could be manufactured of perspex, polycarbonate or other clear material. The nose and/or mouth shield could be adjustable in the vertical direction. This adjustability allows the nose and/or mouth shield to be capable of fitting persons of different facial dimensions. For example the nose and/or mouth shield may include pin(s) and recess(es) as described with reference to the adjustability of the nose pad or other optical elements.

According to a further embodiment, the present invention also includes two arms for retaining the protective eyewear in a substantially fixed position relative to the wearer's head, each arm having a contact portion for contacting the wearer's head towards the rear of the wearer's head, the contact portions being biased towards each other if displaced away from each other from an undisplaced configuration.

Personnel in industrial environments must often wear additional protective equipment such as respirators, ear protection devices, or communication devices the operation of which may be compromised by the location of the arms of eyewear of the prior art. Any seal surrounding the ear may be broken by the arms passing from the inside to the outside of the seal. Additionally, the combination of protective items is often highly uncomfortable for the wearer. Uncomfortable eyewear will often be discarded by workers, defeating the purpose of issuing them with safety equipment.

One of the other problems associated with eyewear of the prior art, is that it is not designed for use in conjunction with heavy optical instruments such as opthalmascopes and magnifying loupes. Somewhat surprisingly, it has been found that such instruments may be magnetically mounted into the modular system of the present invention.

Accordingly, in another embodiment the present invention provides a modular eyewear system comprising:
  a frame member for wearing on a wearer's head, the frame member having magnetic mounting means; and
  a loupe or a similar magnification system, the loupe or magnification system having complementary magnetic mounting means, whereby the loupe or magnification system is releasably mountable to the frame member.
Preferably the loupe or magnification system comprises:
  a first elongate mounting element;
  a pair of magnifying lenses respectively attached at opposite ends of the first mounting element;
  a second mounting element extending from the first mounting element between the magnifying lenses; and
  a connector element attachable to the second mounting element, wherein complementary magnetic mounting means are provided on the connector element.

Preferably, the loupe or magnifying system is also adjustable in various ways to allow it to be tailored to the dimensions of a wearer's head and to take into account the optical effect of other eyewear elements forming part of the modular system, such as prescription lenses. Such adjustability may be provided by magnifying lens that are movable along the first mounting element. The first mounting element may also be rotatable about its longitudinal axis whereby to allow simultaneous vertical movement of both magnifying lenses.

In another embodiment the second mounting element is movable in a substantially vertical direction whereby to allow vertical adjustment of the loupe's position relative to the frame member.

Adjustability may also be provided by a connector element comprising a first part and a second part rotatably attached to the first part to define an axis of rotation substantially parallel to the first mounting element, the loupe being movable by rotation of the second part about the axis of rotation. The second part of the connector element may also be rotatably movable in such a way that the loupe can be displaced from the wearer's field of view. This aspect of the invention is of particular benefit in the surgical environment, as the surgeon need not totally remove the loupe from the system when observation just through the naked eye or prescription lens is required.

The loupe may further include an elongated member extending from the loupe, manual operation thereof allowing rotation of the second part about the said axis of rotation.

In another embodiment the modular eyewear system of the present invention further includes light delivery means for illuminating the subject being viewed through the magnifying lenses of the loupe. When light delivery means are incorporated into the modular system it may be attachable to the loupe so that the illumination direction is in the plane of the axes of the magnifying lenses.

Conveniently, the light delivery means may be illuminated by optical fibre means. Guiding means provided on or attachable to the frame member may also be provided to guide the optical fibre means to the light delivery means.

Heavy optical instruments mounted on conventional frames transmit pressure through the arms of the frames to the unpadded region behind the wearer's ears (the mastoid process). The eyewear can become uncomfortable in use and the frames can tend to slip down the wearer's nose to an optically unsuitable position.

Accordingly, the arms of the present invention are biased towards one another and are wrapped around so as to exert a pressure on the rear wearer's head. This causes the eyewear to be urged towards the wearer's face. This is to be contrasted with prior art spectacle frames in which the frames can tend to fall away from the wearer's face.

Furthermore, use of eyewear according to the present invention having a nose support and arms with contact portions as aforesaid may carry a relatively heavy optical instrument with relatively little discomfort and without the eyewear slipping down the nose allowing use of the optical instrument with greater stability and comfort.

A contact portion according to the present invention may constitute a continuation of the arm with which it is associated. The contact portion may be a spatula. It may be paddle-shaped. Preferably, the contact portion has an elongated surface for contacting the wearer's head. Preferably the contact portion is flat in the vertical direction and curved to approximate the shape of a wearer's head in the horizontal direction; these directions referring to the orientation that the protective eyewear or the platform would assume when worn by a wearer standing upright and looking straight ahead. Preferably, the contact portion has an area of at least 200 mm$^2$ and more preferably it has an area of at least 400 mm$^2$.

Protective eyewear is apt to become fogged. Anti-fogging coatings are known in the prior art, but are a poor solution to the problem since such coatings are quite vulnerable to degradation, rendering them ineffective within a short time. Protective eyewear according to the present invention may include air circulation means for increasing air circulation to the rear of the protective eyewear to prevent fogging. Air circulation means according to the present invention may include one or more rearward projections, whereby eyewear elements are located significantly in front of the nose support to increase the volume of air between the wearer's face and the eyewear element. Air circulation means may include one or more apertures or slots in the eyewear elements to facilitate air flow to the rear of the eyewear element.

The eyewear element may comprise lenses of any convenient material such as glass or plastic or an optical instrument such as an ophthalmoscope or loupe or a light. Where the eyewear element includes lenses, there may be a separate lens for each eye, which may be integrally joined.

The present invention may be used in conjunction with a protective eyeshield, or may use eyewear elements that are protective. Where an eyeshield or eyewear element is protective, to maximize the protection afforded they should fit closely to the wearer's face. They may take any suitable form such as a visor or safety goggles or a wrap around style and side skirts may additionally be provided to provide improved protection against dust, grit, liquids, metal shavings and other foreign matter entering the eye from the side.

The protective eyeshield or protective eyewear element is preferably formed from clear plastics material, although protective eyewear elements of other materials, including tinted shields, polychromatic shields and/or shields made from other materials, are also envisaged within the scope of the present invention. They may include a coating acting as a laser filter. It may be made of a material that acts as a laser filter.

The present invention also provides protective headwear including the eyewear system of the present invention. In a particularly preferred embodiment the headwear comprises a safety helmet including a magnetic mounting means to which eyewear elements may be releasably magnetically mounted. Eyewear according to this embodiment of the invention has no arms or ear pieces to interfere with the operation of ear protection or communication devices covering the ears of a wearer.

The protective headwear may further include a support in the form of a tab. The tab may be configured to extend downwardly from a forward portion of the headwear, and most preferably extends downwardly from a region slightly forward of the region of the wearer's eyes. It is preferred that the support is arranged so as not to obstruct to any significant degree a wearer's straight ahead line of vision. In one embodiment the support lies in a substantially vertical plane transverse to the vertical center line of the wearer's face, the plane being oriented approximately transverse to the wearer's line of sight when looking directly ahead, i.e. approximately parallel to the wearer's forehead. In one particularly preferred embodiment the support comprises a substantially rectangular portion of transparent plastic extending downwardly from a region to the rear of the peak of the headwear in the aforementioned plane.

The support may be secured to the headwear in any suitable manner such as screws, rivets, or by friction or interference fit.

The invention therefore provides a very simple and effective modular eyewear system featuring releasable magnetic mounting of one or more eyewear elements, to a frame member for wearing on a wearer's head. Both the frame member and the eyewear elements are provided with complementary magnetic mounting means, whereby the eyewear element is releasably mountable to the frame member. Other elements of the modular system include light delivery means, eyesight correction lenses, protective eyeshields, adjustable nose-pieces, optical filter elements, masks and helmets, the system allowing these elements to be used separately or together depending on the desired use.

BRIEF DESCRIPTION OF THE DRAWINGS

To further assist in the understanding of the present invention, particularly preferred embodiments of the invention will now be described in relation to the accompanying drawings.

In the drawings, in which like features are indicated by common numerals:

FIG. 1 is a perspective view of a modular eyewear system according to one embodiment of the present invention;

FIG. 2 is a detailed view of the magnetic mounting arrangement for a component in accordance with the embodiment of FIG. 1;

FIG. 3 is a detailed cross-sectional view along the line 3-3 of FIG. 2;

FIG. 10 is a perspective view of a form of magnetic mounting means according to the present invention;

FIG. 11 is a perspective view of part of the eyewear of FIG. 8;

FIG. 12 is a schematic plan view of the manner in which eyewear of FIG. 8 is to be worn;

FIG. 15 is an exploded, perspective view of a further embodiment of a modular eyewear system according to the present invention incorporating a specialist pair of magnifying lenses;

FIG. 16 is a side view of the eyewear and specialist magnifying lenses of FIG. 15;

FIG. 17 is an exploded, perspective view of further embodiment of eyewear according to the present invention incorporating multiple eyewear elements;

FIG. 18 is an exploded side view of the eyewear of FIG. 17;

DETAILED DESCRIPTION OF THE DRAWINGS

Figure 4:
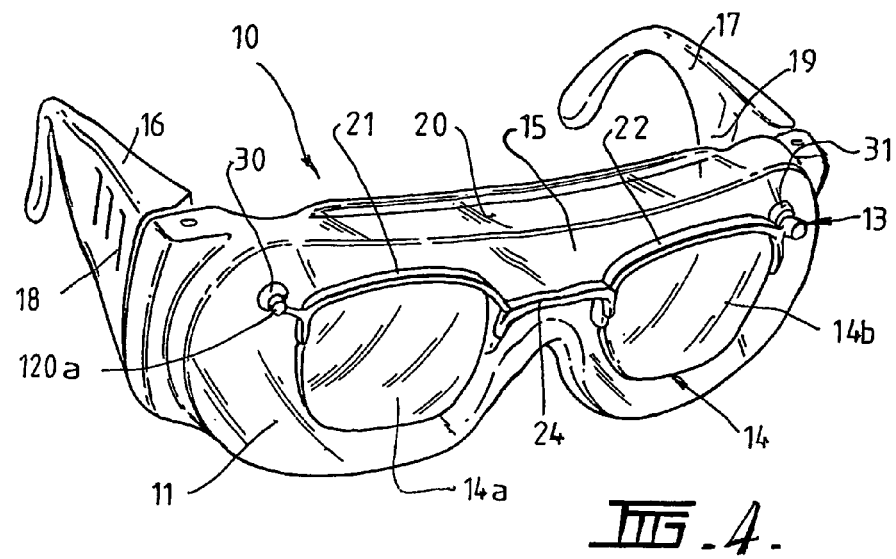
FIG. 4 is a perspective view of the eyewear of FIG. 1 showing an alternative magnetic mounting arrangement for a component according to the invention.

Turning to the drawings, FIGS. 1 to 3 show generally a modular eyewear system 10 in the form of safety goggles including a protective eyeshield 11, a face 15 and arms 16, 17 to attach to the ears of a wearer in a manner known in the art. The modular eyewear system 10 further includes magnetic mounting means 12, 13 for releasable magnetic mounting of an eyewear element 14 to the face 15 of the eyeshield 11.

Eyeshield 11 is intended to wrap around the head of a wearer to provide protection against foreign bodies entering the eye from either side of the wearer or from the top, and includes side skirts 18, 19 and an extended top rail 20.

Eyewear element 14 includes prescription lenses 14a, 14b, lens surrounds 21, 22 and a hinged brow rail 24. Lens surrounds 21, 22 include frame extensions 23 (only one shown in the drawings) at proposed marginal edges of lens surrounds 21, 22. In the embodiment shown in FIG. 2, frame extension 23 comprises an arm terminating in a substantially circular recess in which is held a magnetic mounting member 12a which passes through an aperture 15a in the face of eyeshield 11. On an opposed side of the face 15 is disposed a magnetic disc 12b of opposed polarity to the polarity of magnetic mounting member 12a. When the magnetic mounting member 12a is passed through aperture 15a, the magnetic attraction of magnetic members 12a and 12b as a consequence of their opposed polarity results in the eyewear element 14 being held relative to the face 15 of eyeshield 11.

Figure 5:
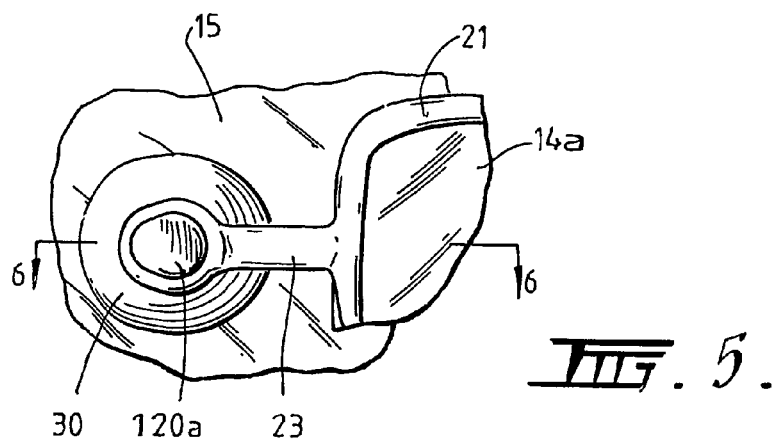
FIG. 5 is a detailed view of an alternative magnetic mounting arrangement in accordance with FIG. 4.
Figure 6:
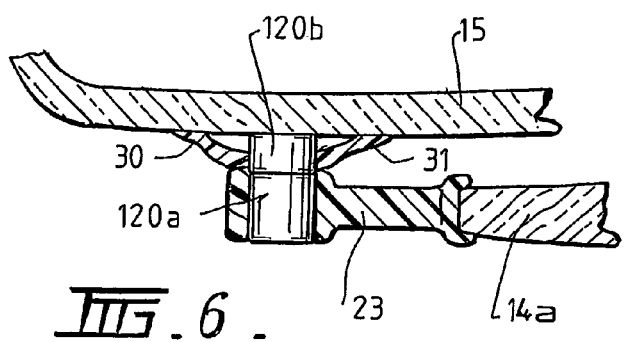
FIG. 6 is a detailed cross-sectional view along the line 6-6 of FIG. 5.

In the embodiment of FIGS. 4 to 6, the magnetic mounting means for releasable magnetic mounting of eyewear element 14 to the eyeshield 11 comprises a two-component mounting means in the form of a cup 120b attached to legs 30, 31 which are in turn attached to the face 15 such as by adhesion, suction or other suitable form of attachment which does not affect the integrity of the face 15. Magnetic mounting member 120a attached to frame extension 23 is of opposed polarity to that of cup 120b such that when magnetic mounting members 120a and 120b are brought into proximity with one another, the magnetic attraction of the mounting members results in the eyewear element 14 being fixed relative to the face 15.

Other magnetic mounting means arrangements and eyewear elements are envisaged within the scope of the present invention.

Figure 7:
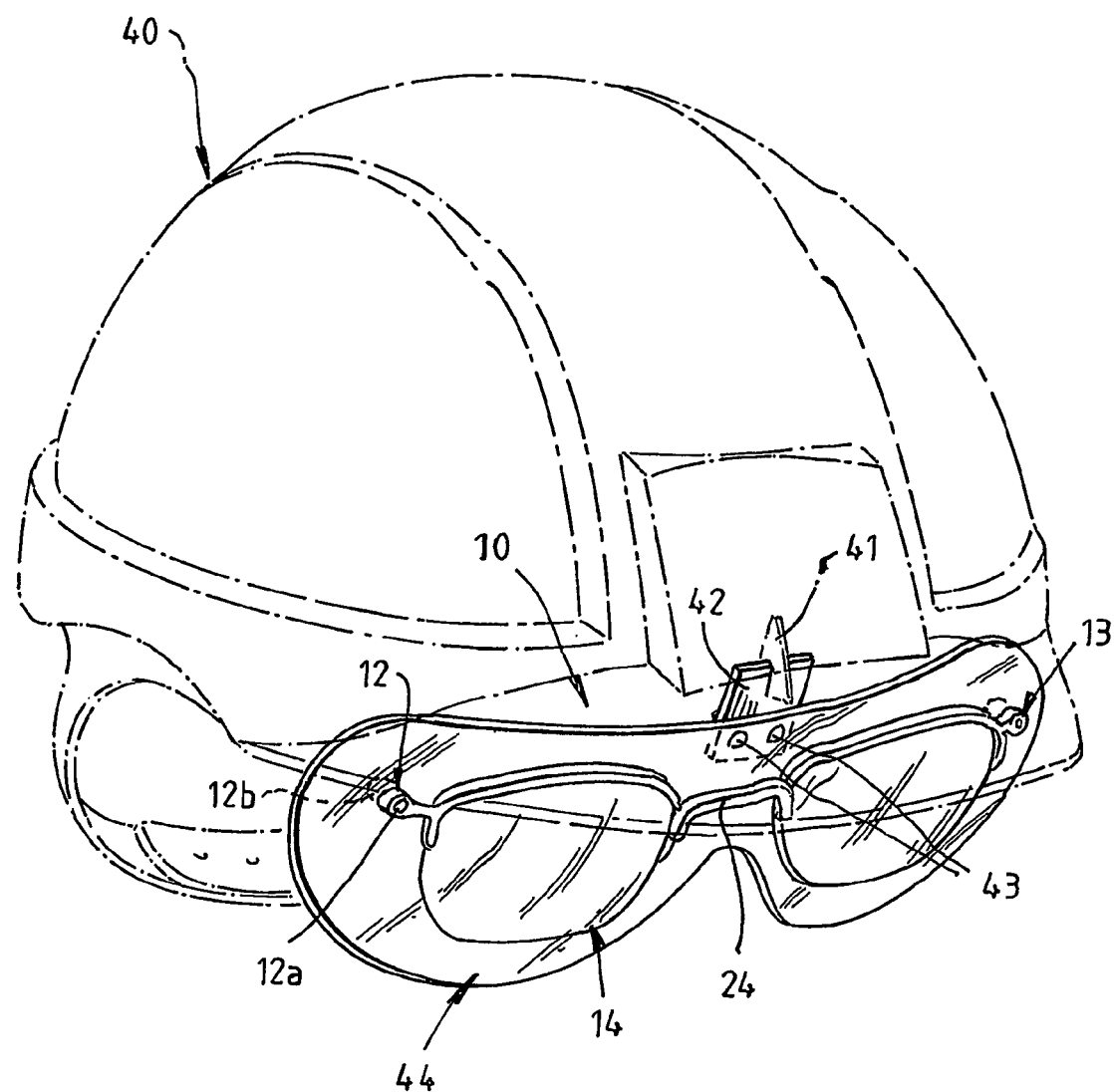
FIG. 7 is a perspective view of an alternative embodiment of the invention applied to protective headwear.
Figure 8:
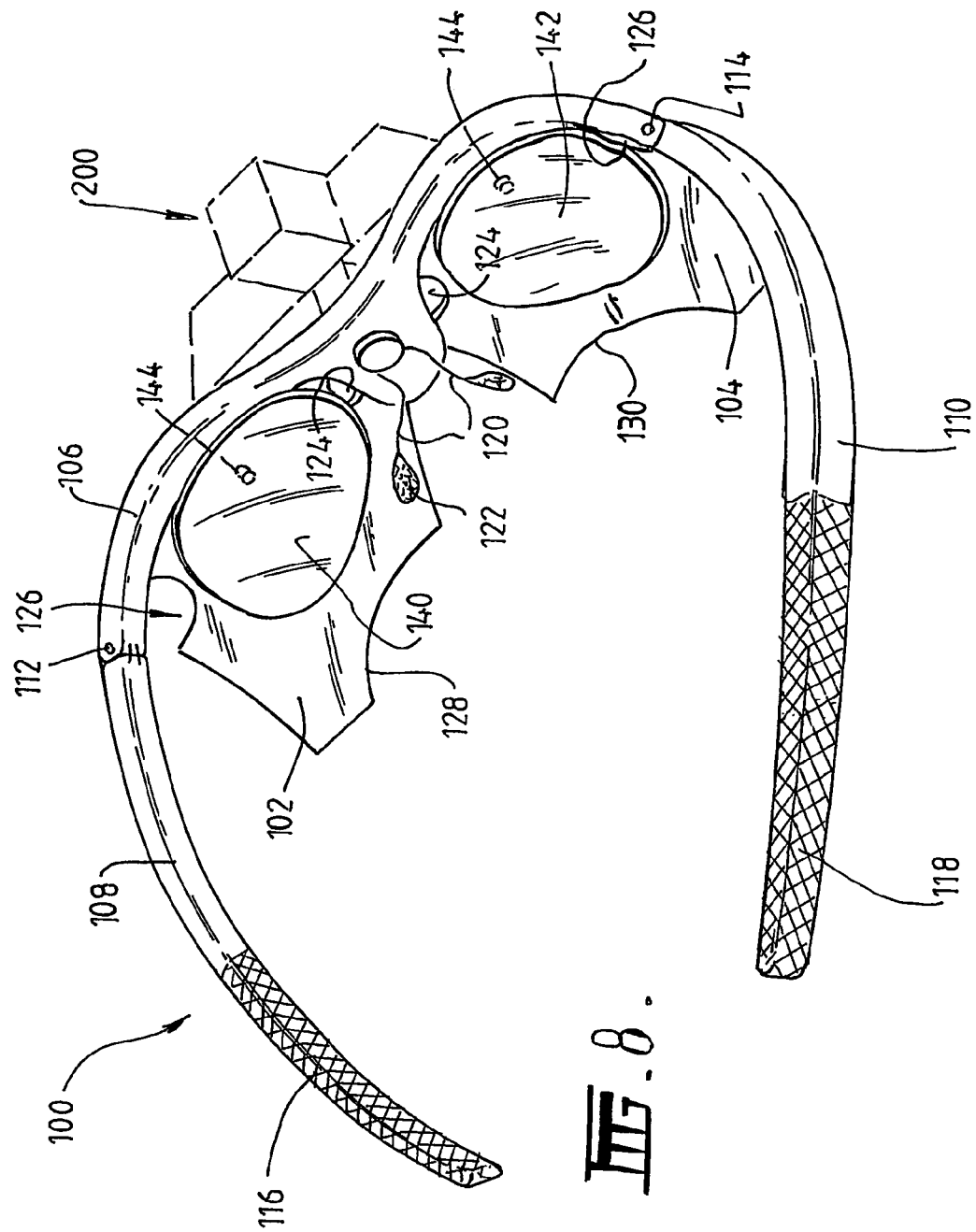
FIG. 8 is a perspective view of a modular eyewear system according to a further embodiment of the present invention.

In the embodiment shown in FIG. 7, the modular eyewear system 10 includes a protective eyeshield 44 (in the form of a visor) and magnetic mounting means 43 for releasable magnetic mounting of the eyeshield 44 to a tab 42 that is connected to protective safety helmet 40. The tab 42 extends downwardly from a region to the rear of the peak of the safety helmet 40 by engagement with a rib 41 carried by safety helmet 40 in that region.

Magnetic mounting means 43 for attachment of the visor to the tab 42 may be as described herein.

An eyewear element in the form of prescription spectacles 14 may also be magnetically mounted to the visor 44 in the manner described herein.

In use, prescription spectacles 14 may be easily demounted from the visor 44 by marginally separating the outer extended frames to overcome the magnetic attraction between the magnetic members of the two component mounting means 12, 13, thereby causing flexing of brow rail 24 which enables the lateral separation of mounting member 12a (or 120a) to clear disc 12b (or cup 120b) as the case may be to overcome the magnetic attraction and thereby remove the prescription spectacles 14 from their mounting on eyeshield 11.

The removal may be effected for cleaning of the prescription spectacles 14 and/or visor 44.

To mount the prescription spectacles 14 the reverse operation may be performed.

The construction and arrangement provided by this embodiment of the present invention is particularly versatile and enables protective eyewear to be provided with eyewear elements such as prescription spectacles which can be easily mounted to the eyeshield or removed from the eyeshield as needed. Thus a modular eyewear system in accordance with this embodiment can be produced economically for use by all with separate prescription lenses provided only to those workers requiring corrective spectacles. In one example of this embodiment the relatively expensive prescription lenses may be easily mounted behind a new eyeshield should any damage occur to the eyeshield.

In the arrangement shown in FIG. 7 a visor 44 is magnetically mounted to the safety helmet 40. The present invention accordingly provides in this embodiment an effective means of providing protective eyewear which does not otherwise interfere with the operation of ear protection or communication or listening devices.

FIGS. 8 to 11 shows a modular eyewear system according to a further embodiment of the present invention. The eyewear system 100 includes a protective eyewear elements in the form of visor pieces 102 and 104. Eyewear 100 also includes a brow rail 106, which is hingedly connected to arms 108 and 110 by hinges 112 and 114.

Arms 108 and 110 have contact portions 116 and 118 respectively.

Figure 9:
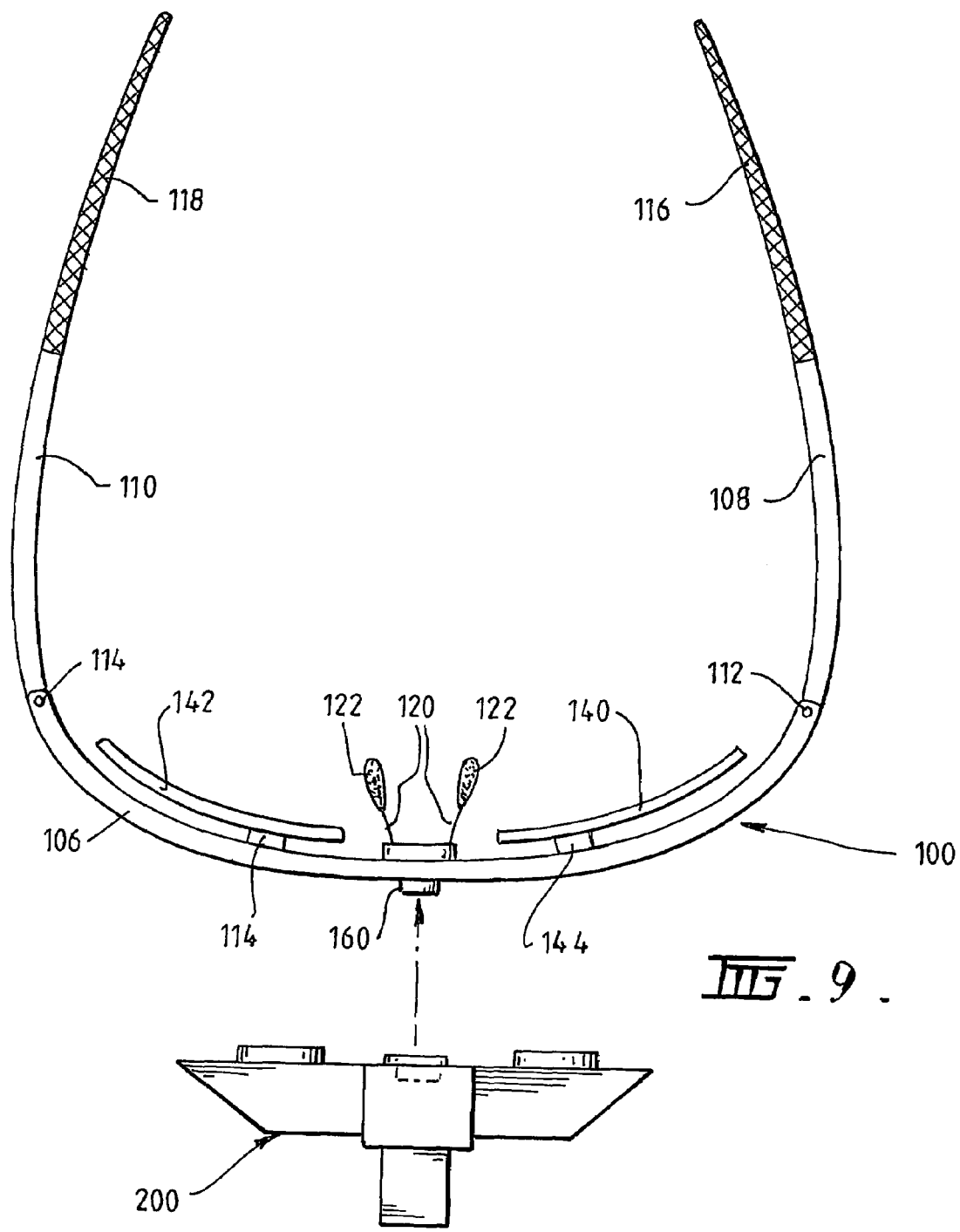
FIG. 9 is a plan view of the eyewear of FIG. 8.

Brow rail 106 is attached to a nose support in the form of supporting rods 120 and nose pads 122, having air circulation means in the form of minus projection for promoting air circulation between the wearer's face and the eyewear (seen most clearly in FIG. 9).

Air circulation means in the form of apertures 124 and slots 126 are also provided to promote air circulation between the wearer's face and the eyewear.

To promote the comfort of the wearer and to ensure the eyewear 100 is not displaced by movement of the wearer's cheeks such as while taking, the bottom edges 128 and 130 of visor pieces 102 and 104 respectively are concave or shaped as if cut away.

The eyewear 100 may include eyewear elements such as prescription lenses 140 and 142. As shown in FIG. 10, visor pieces 102 and 104 may be provided with magnetic mounting means in the form of magnetic cup members 144 for receiving a corresponding magnetic mounting member 146 provided on lenses 140 and 142. Magnetic cups 144 are of opposite polarity to magnetic members 146 so that the magnetic attraction results in lenses 140 and 142 being releasably fixed relative to visor pieces 102 and 104. As will be appreciated, the cup members may be provided on the lenses and the magnetic members for being received in the cup members may be provided on the visor pieces. Alternatively, the point of attachment may be on the brow rail rather than the visor pieces.

Eyewear 100 is also provided with magnetic mounting means for carrying an eyewear element such as optical instrument 200. Brow rail 106 is provided with a projecting magnetic member 160 and a small recess 162. Optical instrument 200 is provided with recess 202 for receiving magnetic member 160, and pin 204 for being received by recess 162. The bottom 206 of recess 202 is magnetic, and of opposite polarity to that of magnetic member 160. The interengagement of member 160 with recess 202, and pin 204 with small recess 162 allows optical instrument 200 to be releasably fixed to brow rail 106 in a manner that prevents rotation of optical instrument 106 with respect to brow rail 106.

In use, as shown in FIG. 12, when eyewear 100 is worn on a wearer's head 300, contact portions 116 and 118 are biased towards each other, the contact portions being displaced apart from one another, in the position shown, from an undeformed position. Consequently, contact portions 116 and 118 tend to try to move towards each other. Because, towards the rear of the head, the head shape converges in a direction approaching the back of the head, if contact portions 116 and 118 were to move towards each other, they would pull the eyewear towards the wearer's face. In this way, eyewear 100 does not have a tendency to slip down the wearer's nose.

In a further embodiment, brow rail 106 is itself magnetic. Components for eyewear such as lenses 140 and 142 and/or optical instrument 200 may be attached to brow rail 106 at a variety of suitable locations. Brow rail 106 may carry projections for being received in recesses in components for eyewear. Components for eyewear may carry projections for being received in recesses in the brow rail 106. Brow rail 106 may have both projections and recesses depending upon the arrangement desired. Brow rail 106 may magnetically releasably be joined to components for eyewear without use of interengaging projections and recesses.

Figure 13:
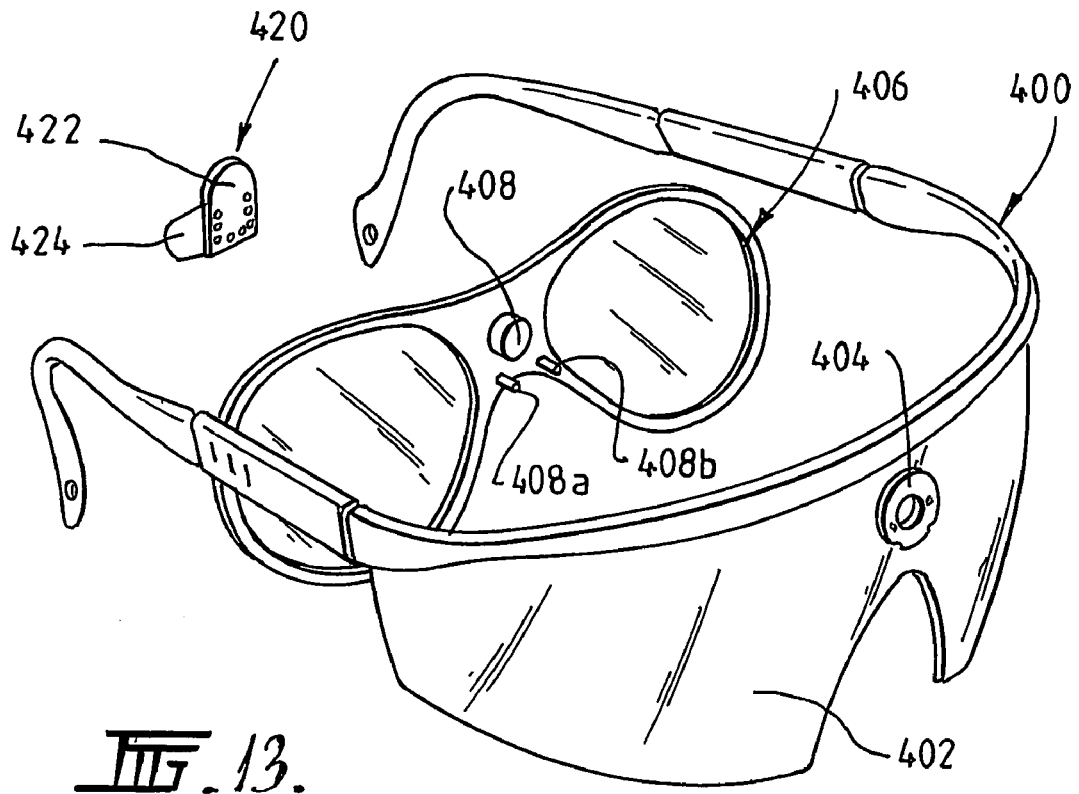
FIG. 13 is an exploded, perspective view of another embodiment of a modular eyewear system according to the present invention.

FIG. 13 shows a further embodiment of a modular eyewear system according to the present invention comprising a protective eyeshield 400 having a visor 402 that fits closely to the wearer's face. In use, an eyewear element 406 in the form of two prescription lenses set in a frame can be located adjacent the visor 402, held in place by virtue of the magnetic attraction between a rare earth magnet 408 on the eyewear element 406 and another magnet 404 on the visor 402. The protective eyewear is also provided with a nose piece 420 which has an extended bridge 422 and nose pads 424, the extended bridge having apertures located along a vertical axis, adapted to receive the locating pins 408a, 408b. Depending on the apertures in which the pins are located, it is possible to optimize the vertical position of the nose piece so that the datum or spectral plane of the prescription lenses are located across the center of the wearer's eyes.

Figure 14:
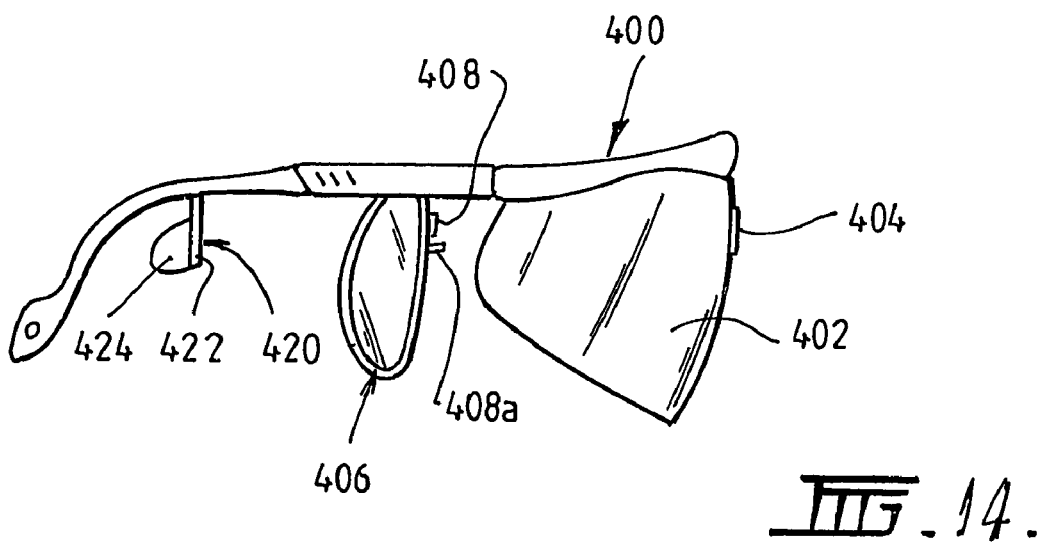
FIG. 14 is a side view of the protective eyewear of FIG. 13.

FIG. 14 is a side view of the protective eyewear of FIG. 13.

FIG. 15 shows a further embodiment of a modular eyewear system according to the present invention comprising a protective eyeshield 450 having a visor 452 that fits closely to the wearer's face. In use, an eyewear element 456 in the form of two prescription lenses set in a frame can be located adjacent the visor 452, held in place by virtue of the magnetic attraction between a rare earth magnet 458 on the eyewear element 456 and a lens fixing plate 454 on the visor 452 which is held in place by screws passing through corresponding recesses 460a and 460b. An O-ring 459 is located between the two magnets. In addition, a locating pin 457, passes through recess 461, holding the eyewear element in place and preventing rotation relative to the visor. The eyewear is also provided with a nose piece 470 which has an extended bridge 472 and nose pads 474, the extended bridge having apertures located along a vertical axis, adapted to receive the locating pin 457. Depending on the apertures in which the locating pin 457 is located, it is possible to optimize the vertical position of the nose piece so that the datum or spectral plane of the prescription lenses are located across the center of the wearer's eyes. Also shown is a magnification device 476 having two magnifying eyepieces 476a, 476b and an extended bridge having apertures located along a vertical axis, adapted to receive the locating pin 457. Again, depending on the aperture in which the locating pin is located, it is possible to optimize the vertical position of the eyepieces.

FIG. 16 is a side view of the protective eyewear and specialist magnifying lenses of FIG. 15.

FIG. 17 is an exploded, perspective view of another embodiment of a modular eyewear system 518 according to the present invention comprising a frame member 500 which in use is attached to a prescription lens holder 502 by the attraction between a rare earth magnet 504 on the lens holder 502, and a tab 512 on the frame member 500. An O-ring 516 is located between the rare earth magnet 504 and the tab 512. The frame member also includes two projections 502a, 502b which can be located in corresponding apertures in the extended bridge 522 of a nose piece 520. The choice of apertures in which the pins are located, will affect the position in which the nose pad 524, and the frame member 500, sit in relation to the eyes of the wearer. Replaceable eyewear elements can be held in place in relation to the frame member 500 between the tab 512, and a fixing plate 510 and located in position on the outer most eyewear element 532 by a pair of screws. In this embodiment the eyewear elements include a coloured ski shield 528, a polarising gold lens 530 and a polarising grey lens 532. The second magnet can be readily manually removed to allow one or more elements to be disengaged from the projections 518a, 518b, and replaced by one or more other eyewear elements. The frame also includes a small LED light source to provide the wearer with illumination for reading or close work.

FIG. 18 is an exploded side view of the eyewear of FIG. 17.

Figure 19:
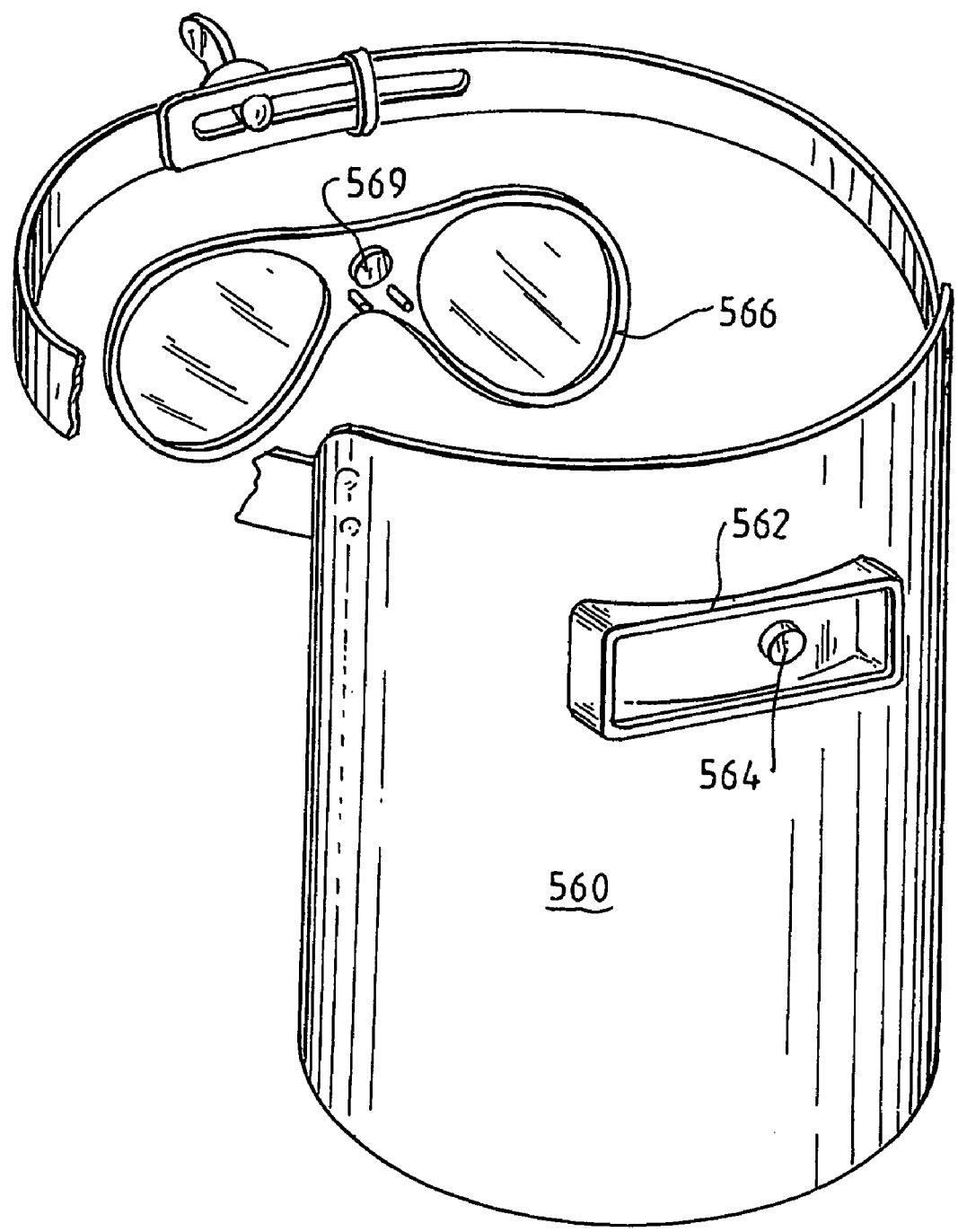
FIG. 19 is a view of an embodiment of a welding shield adapted for use with the present invention.

FIG. 19 shows a welding shield including a full opaque visor 560 for protecting the face and neck of a welder and a thick, tinted glass viewing window 562 through which the welder can observe the welding work. The window 562 has been adapted to include a small magnet 564. In use an eyewear element 566 in the form of a pair of framed prescription lenses, is held in position against the window by the magnetic attraction between the magnet on the window 562 and a second magnet 569 on the eyewear element. Thus the welder does not need to have a special, prescription ground window incorporated into the welding shield at great cost, and thus limiting the use of the shield to the sole person for whose eyesight the window has been adapted.

Figure 20:
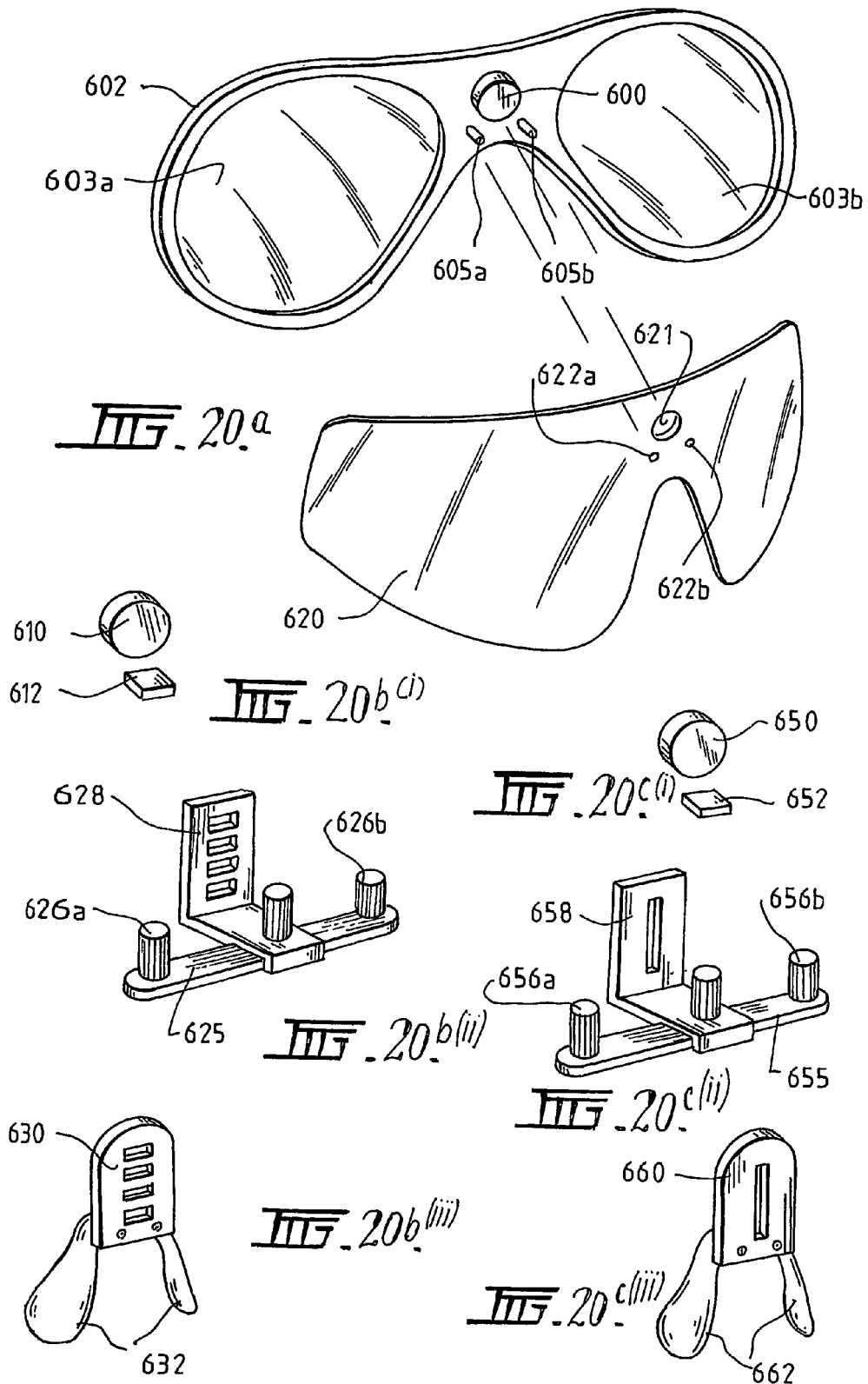
FIG. 20 is a view of two different embodiments of the magnetic mounting means according to the present invention.

FIG. 20 shows two different embodiments of the magnetic mounting means of the present invention. FIG. 20a depicts an embodiment of the magnetic mounting means as described in relation to FIGS. 13 to 19, that is a small, disc shaped, rare earth magnet 600 and two pin-like projections 605a, 605b located in a frame 602 holding two lenses 603a, 603b. The combination of magnet and projections can be used for locating the frame in relation to an eyewear element 620. In use, the rare earth magnet is located in circular recess 621 in the eyewear element 620 and the pin-like projections 605a, 605b are located in the recesses 622a and 622b.

FIG. 20b(i) depicts another embodiment of the magnetic mounting means comprising a small, disc shaped, rare earth magnet 610 and a rectangular projection 612. FIG. 20b(ii) depicts a platform 625 on which can be mounted one or two magnifying lenses or the like. The magnifying lenses can be adjusted using rotatable knobs 626a, 626b. The platform includes a bridge piece 628 having rectangular recesses which are of complementary shape to the projection 612 of FIG. 20b(i). Thus, by inserting the projection 612 into the appropriate recess, the position of the platform can be optimised relative to the rest of the eyewear. Similarly, the nosepiece 630 of FIG. 20b(iii) includes rectangular shaped recesses in a bridge piece 630. By inserting the projection 612 of FIG. 20b(i) into the appropriate recess, the position of the nosepads 632, and thus the entire eyewear, can be optimised.

FIG. 20(c)(i) depicts another embodiment of the magnetic mounting means comprising a small, disc shaped rare earth magnet 650 and a rectangular projection 652. FIG. 20(c)(ii) depicts a platform 655 on which can be mounted one or two magnifying lenses or the like. The magnifying lenses can be adjusted using rotatable knobs 656a, 656b. The platform includes a magnetic bridge piece 658 having a single, slot-like recess which is of similar width to the projection 652 of FIG. 20(c)(i). Thus the projection 652 can be slid up and down in the recess to optimise the position of the platform relative to the rest of the eyewear. Similarly, the nosepiece 660 of FIG. 20(c)(iii) includes a slot-like recess in a magnetic bridge piece 660. By sliding the projection 652 of FIG. 20(c)(i) along the slot-like recess the position of the nosepad 662, and thus the entire eyewear, can be optimized. Use of a slot-like recess is particularly effective if it is used in combination with a very strong rare earth magnet, and the slot is located in metal that is strongly attracted to the metal so that the projection is firmly held in position in the recess.

Figure 21:
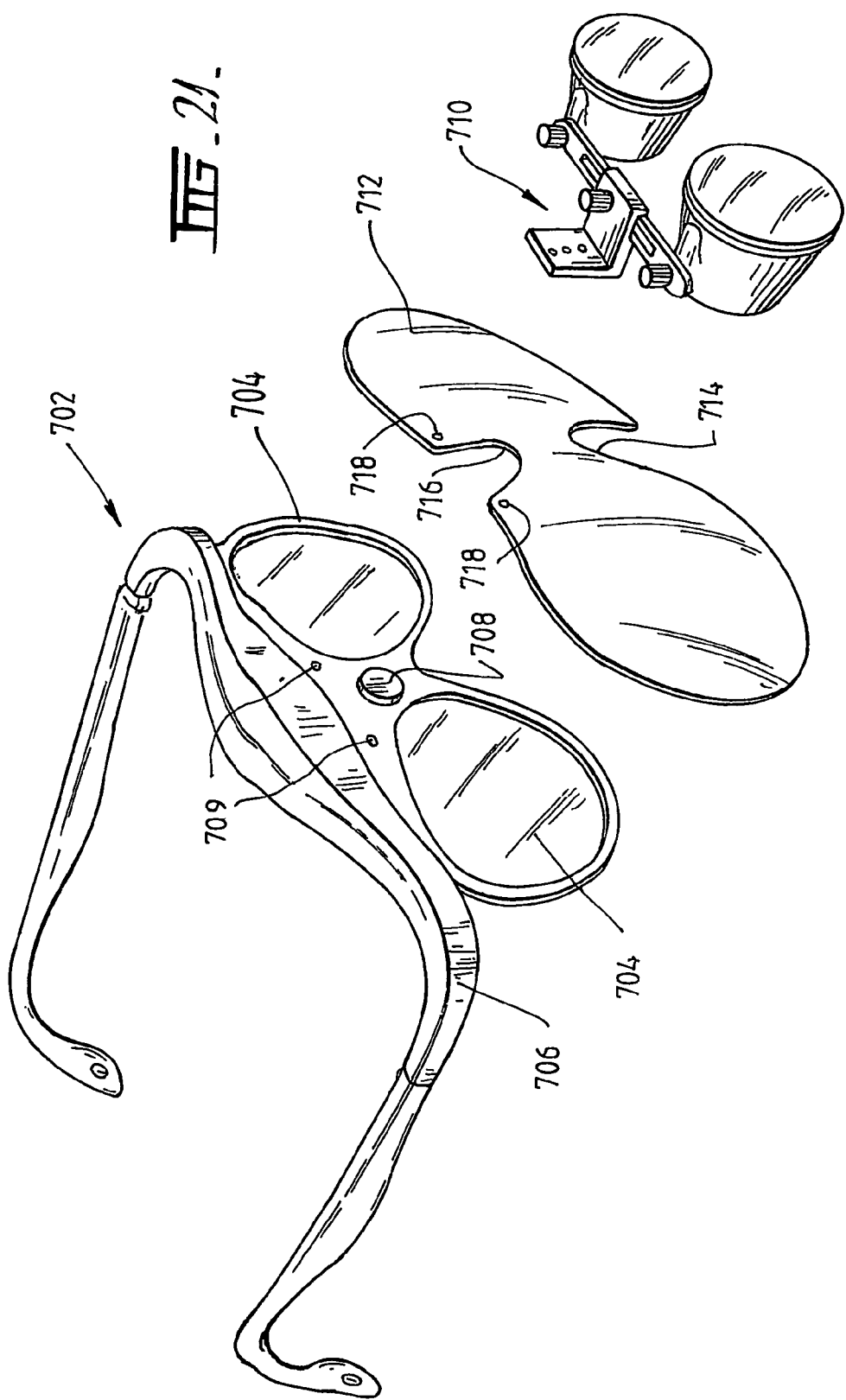
FIG. 21 is a perspective view of another embodiment of a modular eyewear system according to the present invention.

FIG. 21 shows an exploded perspective view of another embodiment of a modular eyewear system according to the present invention. This embodiment is similar to that described by reference to FIG. 17, except that the prescription lenses 704 (and lens holder) are permanently attached to frame member 706 rather than being removably attached thereto by way of magnetic attraction. A rare earth magnet 708 and a pair of spaced projecting locating pins 709 are also provided on the lens holder as shown, to afford location and attachment of a protective shield 712 by insertion of pins 709 through apertures 718 in shield 712. Shield 712 is formed with an upper recesses 716 that exposes magnet 708 after location of shield 712, to allow mounting of an optical instrument 710, which includes a magnet of opposite polarity to rare earth magnet 708.

Protective shield 712 is therefore readily replaceable, and serves to protect the lenses 704 and the face of the wearer from contamination, such as that which might occur during surgery. Shield 712 can be simply and rapidly removed or replaced by decoupling and recoupling the magnetic connection of the eyewear system as and when required.

Figure 22:
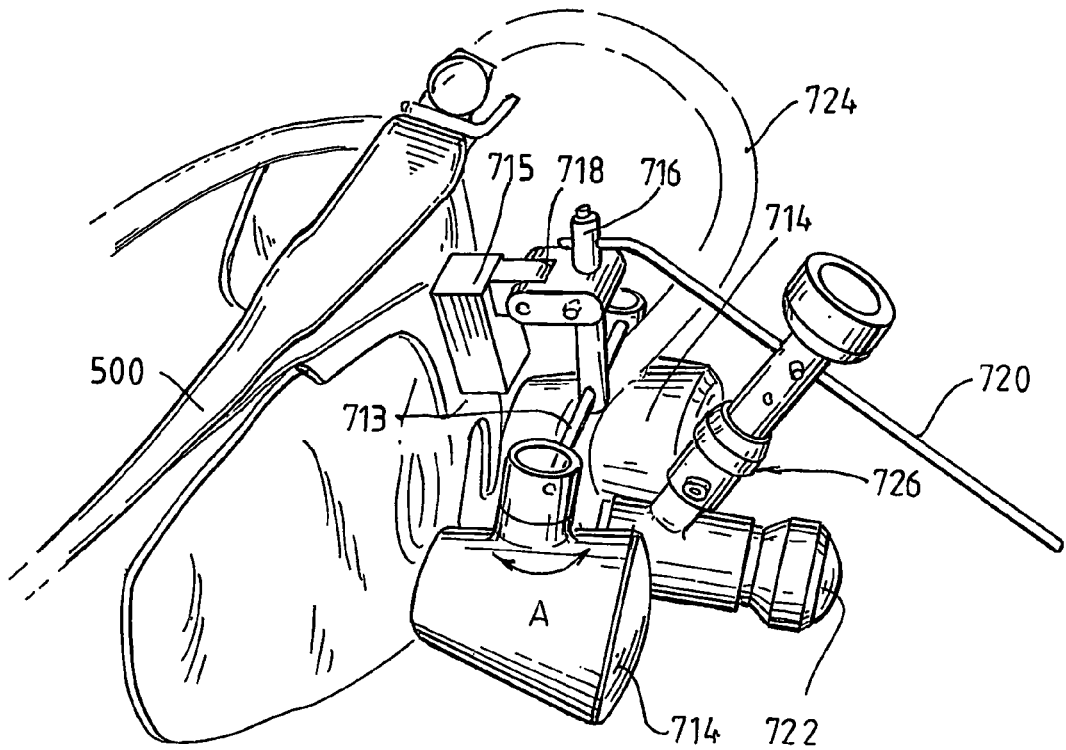
FIG. 22 is a perspective view of a further embodiment of the present invention illustrating the incorporation of a loupe into the modular system.

As shown in more detail in FIG. 22 optical instrument 710 is a binocular magnifying loupe or similar, for use by practitioners such as surgeons, dentists or jewellers. It comprises a first rod-form elongate mounting element 713 which has a pair of magnifying lenses 714 respectively attached to the opposite ends thereof. Each of the magnetic lenses is individually rotatable about element 713 and moveable thereaulong, so allowing rotational movement of the elements (indicated by arrow A in FIG. 22) and translational displacement therebetween. Grub screws allow the lenses to be fixed into desired positions once adjusted.

A second rod-form elongate mounting element 716 extends from the first element 713 between the magnifying lenses and attaches to a pivoting connector element 718. The element 713 passes through and is rotatably mounted in a horizontal bore through element 716 as shown (and fixable by means of a grub screw), so that the lens assembly can be rotated about the horizontal transverse axis (arrow A). As shown, element 716 passes through an approximately vertical bore in element 718 and is fixable therein be means of a grub screw, affording vertical adjustment of the magnifying lens assembly. The connector element 718 in turn, mounts the loupe 710 to the frame member 500 by way of a recessed magnet (not shown in FIG. 22) providing the magnetic mounting means on the loupe that attach to the complementary rare earth magnet projecting from the frame member.

Figure 23:
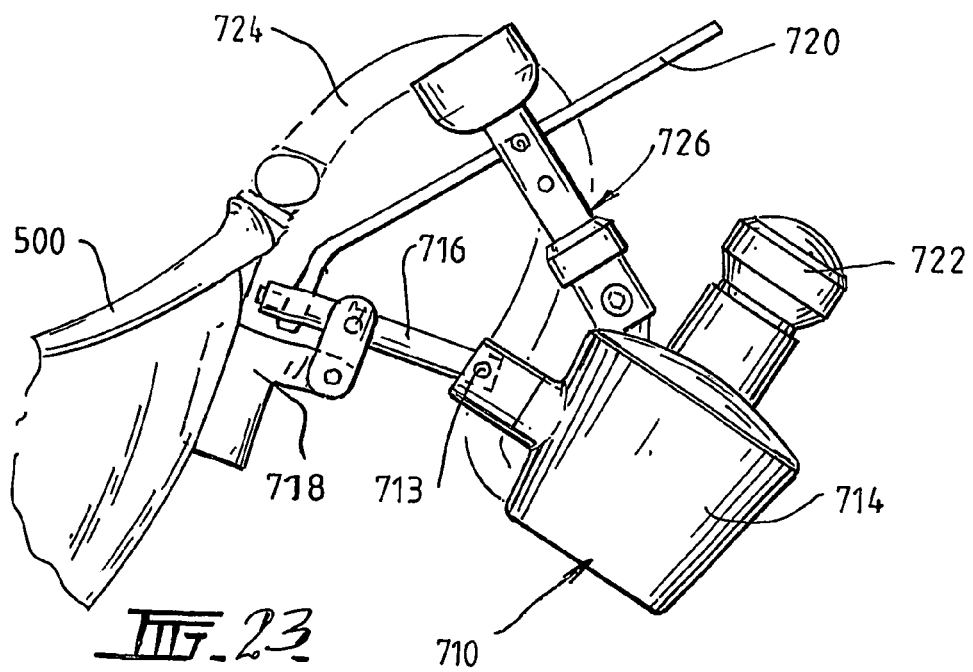
FIG. 23 is a side view of the loupe illustrated in FIG. 22 in a position displaced from the wearer's field of view.

The pivoting connector element 718 comprises a first part 715 upon which the magnetic mounting means are provided and a second part 716 that is pivotally attached to the first part by way of a hinge. The connector element imparts additional flexibility to the loupe by defining a second axis of rotation, substantially parallel to the axis provided by the first mounting element 713, about which the loupe assembly may be rotated. In use, this allows the loupe to be quickly and easily removed from a wearer's field of vision, as may be required during a surgical procedure. As illustrated in FIG. 23, the loupe is displaceable from the field of view by manual operation of a projecting handle 720, fixably attached to the upper end of element 716. The hinge assembly of element 718 may provide a two-position bias for the loupe assembly, or may provide sufficient resistance such that the wearer can simply move the loupe assembly into any desired position by way of handle 720. FIG. 23 shows the loupe assembly raised out of the wearer's field of vision.

The modular system may also incorporate light delivery means in the form of a bulb or lens 722 for illuminating the subject being viewed through the magnifying lenses 714, such as during a surgical procedure. Illumination is provided by an optical fibre means 724. In the illustrated embodiment the bulb is mechanically attached to the loupe by way of a bore therein through which the third elongated member 720 passes (and is secured thereto by means of a grub screw). The light delivery means is also equipped with magnetic mounting means 726, being a recessed magnet, to allow magnetic coupling of the bulb 722 into the modular system. In this way, the light delivery means may be magnetically mounted to a complementary magnet projecting outwardly from element 715, or may be mounted directly to the magnet projecting from the frame member if the user is not using the loupe. The modular system therefore permits simple assembly of the different eyewear components depending on the particular use required. Where the modular system incorporates both a loupe and light delivery means, it is preferred that they be located such that the direction of illumination lies in the plane of the wearer's view (the axes of lenses 714) as illustrated by the dotted arrows in FIG. 22.

Whilst it has been convenient to describe the present invention in relation to particularly preferred embodiments, it is to be appreciated that other constructions and arrangements are considered as falling within the scope of the invention. Various modifications, alterations, variations and/or additions to the constructions and arrangements described herein are considered as falling within the scope of the present invention.

The invention claimed is:

1. A modular eyewear system including magnetic mounting means for releasable magnetic mounting of one or more eyewear elements comprising:
   a frame member for wearing on a wearer's head, the frame member having magnetic mounting means; and
   a loupe or a similar magnification system, the loupe or magnification system having complementary magnetic mounting means, whereby the loupe or magnification system is releasably mountable to the frame member.

2. A modular eyewear system according to claim 1 further including mechanical mounting means for releasable mechanical mounting of eyewear elements in addition to the magnetic mounting of eyewear elements.

3. A modular eyewear system according to claim 2 wherein the mechanical mounting means allows the location of an eyewear element to be adjusted to a plurality of positions relative to one or more other eyewear elements.

4. A modular eyewear system according to claim 2 wherein the mechanical mounting means is a locating pin and recess.

5. A modular eyewear system according to claim 1 wherein the loupe or magnification system comprises:
   a first elongate mounting element;
   a pair of magnifying lenses respectively attached at opposite ends of the first mounting element;
   a second mounting element extending from the first mounting element between the magnifying lenses; and
   a connector element attachable to the second mounting element, wherein complementary magnetic mounting means are provided on the connector element.

6. A modular eyewear system according to claim 5 wherein each magnifying lens is movable along the first mounting element.

7. A modular eyewear system according to claim 5 wherein the first mounting element is rotatable about its longitudinal axis to allow simultaneous movement of both magnifying lenses.

8. A modular eyewear system according to claim 5 wherein the second mounting element is movable in a substantially vertical direction to allow vertical adjustment of the position of the loupe or magnification system relative to the frame member.

9. A modular eyewear system according to claim 5 wherein the connector element comprises a first part and a second part rotatably attached to the first part to define an axis of rotation substantially parallel to the first mounting element, the loupe or magnification system being movable by rotation of the second part about the axis of rotation.

10. A modular eyewear system according to claim 9 wherein the second part is rotatably movable in such a way that the loupe or magnification system can be displaced from the wearer's field of view.

11. A modular eyewear system according to claim 9 wherein the loupe or magnification system further includes an elongated member extending from it, manual operation thereof allowing rotation of the second part about the said axis of rotation.

12. A modular eyewear system according to claim 1 further including light delivery means for illuminating the subject being viewed through the loupe or magnification system.

13. A modular eyewear system according to claim 12 wherein the light delivery means is attachable to the loupe or magnification system so that the illumination direction is in the plane of the axes of the magnifying lenses.

14. A modular eyewear system according to claim 12 wherein the illumination is provided by optical fibre means.

15. A modular eyewear system according to claim 14 including guiding means provided on or attachable to the frame member for retaining the optical fibre means.

16. A modular eyewear system according to claim 1, including a nose support which is releasably mountable to an eyewear element by way of the magnetic mounting means.

17. A modular eyewear system according to claim 16 wherein the nose support is mountable to the eyewear element in a plurality of positions, in order to adjust the vertical position of the eyewear element on the wearer's head.

18. A modular eyewear system according to claim 1, including a pair of arms for retaining eyewear elements in a substantially fixed position relative to the wearer's head, the arms being biased towards one another and curved to wrap around the wearer's head to exert pressure on the rear of the head, thereby urging the eyewear elements toward the wearer's face.

19. A modular eyewear system according to claim 1, wherein the magnetic mounting means comprises a magnetic projection and a cooperating magnetic recess.

20. A modular eyewear system according to claim 1, including means for attaching further eyewear elements including any one or more of lenses, protective shields, optical instruments and illumination devices.

21. A modular eyewear system according to claim 1, comprising:
   a frame member for wearing on a wearer's head;
   a lens holder permanently attached or integrally formed with the frame member, the lens holder having magnetic mounting means and locating pins disposed thereon; and
   an eyewear element having complementary magnetic mounting means provided thereon for releasable magnetic mounting of the eyewear element to the frame member whereby a protective shield having apertures therein may be interposed between the eyewear element and the frame member.

22. A modular eyewear system according to claim 1, wherein one or more of the eyewear elements include air circulation means for increasing air circulation to the rear of the eyewear elements to prevent fogging.

23. A modular eyewear system according to claim 22, wherein the air circulation means comprises one or more apertures or slots in the eyewear elements or other elements.

* * * * *